United States Patent [19]

Chin et al.

[11] Patent Number: 5,420,360
[45] Date of Patent: May 30, 1995

[54] PROCESS FOR THE CONVERSION OF C5 LINEAR OLEFINS TO TERTIARY ALKYL ETHERS

[75] Inventors: Arthur A. Chin, Cherry Hill; Roland B. Saeger, Runnemede, both of N.J.; James A. Stoos, Beaumont, Tex.; Robert A. Ware, Wyndmoor, Pa.

[73] Assignee: Mobil Oil Corporation, Fairfax, Va.

[21] Appl. No.: 112,286

[22] Filed: Aug. 27, 1993

[51] Int. Cl.$^6$ .............................................. C07C 41/06
[52] U.S. Cl. .................................................... 568/697
[58] Field of Search ......................................... 568/697

[56] References Cited

U.S. PATENT DOCUMENTS

| | | | |
|---|---|---|---|
| 4,605,787 | 8/1986 | Chu et al. | 568/697 |
| 4,788,365 | 11/1988 | Harandi et al. | 585/312 |
| 4,826,507 | 5/1989 | Harandi et al. | 44/77 |
| 4,854,939 | 8/1989 | Harandi et al. | 44/77 |
| 5,132,467 | 7/1992 | Haag et al. | 568/697 |
| 5,136,108 | 8/1992 | Gaffney et al. | 568/697 |
| 5,166,455 | 11/1992 | Chin et al. | 568/697 |
| 5,210,327 | 5/1993 | Luebke et al. | 568/697 |

FOREIGN PATENT DOCUMENTS 0026041 4/1981 European Pat. Off.
0247802 12/1987 European Pat. Off.

*Primary Examiner*—Alan Siegel
*Attorney, Agent, or Firm*—Alexander J. McKillop; Dennis P. Santini; Laurence P. Hobbes

[57] ABSTRACT

A process is disclosed for producing alkyl tertiary alkyl ether such as TAME from alkanol and hydrocarbon feedstock containing linear olefins, iso-olefins, linear alkanes and iso-alkanes such as C5 streams from FCC. The process selectively etherifies iso-olefins in a plural stage etherification zone whose linear olefin-containing effluent is treated by distillation to remove iso-alkanes, and alkanol before passing to a skeletal isomerization zone using constrained intermediate pore size zeolite catalyst such as ZSM-22, ZSM-23, or ZSM-35, which converts linear olefins to iso-olefins which are cycled for etherification. The use of distillation to remove iso-alkanes and alkanol reduces mass flow to the etherification process and minimizes skeletal isomerization catalyst poisoning by alkanol, without resort to water extraction processes which require subsequent treatment of the isomerization zone feed to remove water.

18 Claims, 5 Drawing Sheets

PROCESS FOR THE CONVERSION OF C5 LINEAR OLEFINS TO TERTIARY ALKYL ETHERS

This invention relates to an integrated process for the production of alkyl tertiary alkyl ethers. The invention particularly relates to an integrated process for converting a feedstock containing linear olefins and iso-olefins to high octane tertiary alkyl ethers. More particularly, the invention relates to the conversion of linear and branched alkenes in C5 or C5+ feedstock to C5+ gasoline components containing tertiary amyl methyl ether (TAME).

BACKGROUND OF THE INVENTION

It is known that isopentene and other isoalkenes, or iso-olefins, produced by hydrocarbon cracking may be reacted with methanol and other C1–C4 lower aliphatic alcohols, or alkanol, over an acidic catalyst to provide tertiary amyl methyl ether (TAME) or the like. Generally, it is known that asymmetrical ethers having the formula $(CH_3)_3C-O-R$ where R is a C1–C4 alkyl radical, are particularly useful as octane improvers for liquid fuels, especially gasoline.

MTBE, ethyl t-butyl ether (ETBE), tert-amyl methyl ether (TAME) and isopropyl t-butyl ether (IPTBE) are known to be high octane ethers. The article by J. D. Chase, et al., *Oil and Gas Journal*, Apr. 9, 1979, discusses the advantages one can achieve by using such materials to enhance gasoline octane.

The reaction of tertiary olefins with alkanol to produce alkyl tertiary alkyl ether is selective with respect to iso-olefins. Linear olefins are unreactive in the acid catalyzed reaction, even to the extent that it is known that the process can be utilized as a method to separate linear and iso-olefins. The typical feedstream of FCC C5 or C5+ crackate used to produce tertiary alkyl ethers in the prior art and containing normal pentenes and isopentenes utilizes only the tertiary olefin in etherification. This situation presents an exigent challenge to workers in the field to discover a technically and economically practical means to utilize linear olefins, particularly normal pentenes, in the manufacture of tertiary alkyl ethers.

European Patent 0026041 to Garwood, incorporated herein by reference, discloses a process for the restructuring of olefins in contact with zeolite catalyst to produce iso-olefins, followed by the conversion of iso-olefins to MTBE and TAME. The restructuring conditions comprise temperature between 204° C. and 315° C. and pressure below $5.1 \times 10^4$ Pa. In European Patent 0247802 to Barri et al, it is taught that linear olefins can be restructured in contact with zeolite catalyst, including ZSM-23, to produce branched olefins. The restructuring conditions comprise temperature between 200°–550° C., pressure between 100 and 1000 MPa and WHSV between 1 and 100. It is taught that in the process 1-butene conversion exceeds 59 mole % with a selectivity to isobutene greater than 52 mole %.

It has been discovered that under certain conditions substantial improvements in the art of alkyl tert-alkyl ether production can be realized in a combination or integration of etherification and hydrocarbon conversion processes based upon zeolite type catalysis. In U.S. Pat. Nos. 4,788,365, 4,826,507 and 4,854,939 to M. N. Harandi and H. Owen novel processes are described for carrying out the production of MTBE and TAME wherein unreacted alcohol and light olefin components from the etherification reaction are converted to higher hydrocarbons in contact with zeolite catalyst. These patents are incorporated herein by reference. In these processes the etherification reaction is carried out using C4+ hydrocarbon feedstream rich in iso-olefins with the subsequent oligomerization of unreacted light olefins.

U.S. Pat. No. 4,605,787 to Chu et al., incorporated herein by reference, describes a process for the preparation of methyl tertiary butyl ether which comprises reacting isobutylene and methanol in the vapor phase in the presence of zeolite catalyst. Under the conditions described for the vapor phase etherification, side reactions, particularly the dimerization of isobutylene, are virtually eliminated. The reaction products are essentially MTBE and unreacted methanol and/or isobutylene.

U.S. Pat. No. 5,132,467 to Haag et al., incorporated herein by reference, describes a process for producing tertiary alkyl ethers wherein linear olefins are isomerized in the vapor phase to produce iso-olefin vapor which is etherified to form MTBE. Unreacted iso-olefin and/or linear olefin and product ether are separated by fractionation using fresh feed as a reflux stream to the fractionator and unreacted olefin components recycled.

U.S. Pat. No. 5,210,327 to Luebke et al., incorporated herein by reference, describes an etherification process and a process for isomerizing linear alkenes in the etherification effluent to isoalkenes. The process uses a distillation separation zone for the etherification effluent from which is taken an overhead rich in isopentane and a side cut comprising linear olefins which is cycled to a skeletal isomerization unit. The process provides for recycle of linear olefins while maintaining low mass flow through the isomerization zone by eliminating isopentane from the isomerization zone recycle feed. The process separates alkanol from the feed to the isomerization unit by interposing a water wash column to separate out methanol requiring further treatment of the feed to remove residual water and oxygenates.

It is an object of the present invention to provide a process for the etherification of linear olefins, particularly n-pentenes, to alkyl tertiary alkyl ether, particularly TAME.

It is another object of the invention to provide a process for the isomerization of linear olefins to iso-olefins followed by the etherification of the iso-olefins so formed to provide alkyl tert-alkyl ethers.

Yet another object of the instant invention is to provide an integrated process for the etherification of linear and branched olefin components of a hydrocarbon feedstream by combining sequential etherification reactions with linear olefin isomerization to produce alkyl tert-alkyl ether, particularly TAME, while minimizing mass flow to the etherification reactors by employing distillation to provide an alkanol-free, water-free olefin recycle stream to the isomerization reactor without using alkanol/water extraction of the stream and subsequent alkanol/water separation, thereby increasing the yield of ether on fresh feed with minimal expansion of the etherification reactors.

Still another objective of the present invention is to provide an integrated process for the plural stage etherification of linear and branched olefin components of a hydrocarbon feedstream by combining sequential etherification reactions with linear olefin isomerization to produce alkyl tert-alkyl ether, wherein the mole ratio of alkanol to iso-olefins in the first etherification stage is maintained at greater than 1 to provide higher conversion of iso-olefins to ether, while excess alkanol is reacted in subsequent etherification stage(s) with iso-olefins obtained from isomerization of linear olefins, to maximize ether production from a feed containing linear and iso-olefins.

Another objective of the present invention is to provide an integrated process for the plural stage etherification of linear and branched olefin components of a hydrocarbon feedstream by combining sequential etherification reactions with linear olefin isomerization to produce alkyl tert-alkyl ether, wherein the overhead effluent of the final etherification zone is separated by distillation to linear olefin-rich recycle stream and an overhead stream containing iso-pentane and only minor amounts of methanol and water, said overhead stream being suited to direct incorporation in a refinery gasoline pool.

SUMMARY OF THE INVENTION

The present invention relates to a process for producing alkyl tertiary alkyl ether such as TAME or MTBE from alkanol and hydrocarbon feedstock containing linear olefins, iso-olefins, linear alkanes and iso-alkanes such as C4+, C5, or C5+ streams from FCC. The process selectively etherifies iso-olefins in plural stage etherification zones whose linear olefin-containing effluent is treated by distillation to remove iso-alkanes, alkanol, and water if present, before passing to a skeletal isomerization zone using constrained intermediate pore size zeolite catalyst such as ZSM-22, ZSM-23, or ZSM-35, which converts linear olefins to iso-olefins which are cycled for etherification. The use of distillation to remove iso-alkanes and alkanol reduces mass flow to the etherification process and prevents skeletal isomerization catalyst poisoning by alkanol, without resort to water extraction processes which require subsequent treatment of the isomerization zone feed to remove water.

In one embodiment, the present invention relates to a continuous integrated process for producing alkyl tertiary alkyl ether from alkanol and hydrocarbon feedstock containing linear olefins, iso-olefins, linear alkanes and iso-alkanes. The process comprises:

(a) contacting said alkanol and said hydrocarbon feedstock with acid etherification catalyst under iso-olefin etherification conditions in a first etherification reaction zone;

(b) passing at least a portion of the effluent from said first etherification reaction zone which effluent comprises ether, alkanol, iso-olefins, linear olefins, linear alkanes and iso-alkanes to a second etherification reaction zone which is a reactive distillation zone and withdrawing from said zone a high boiling fraction comprising said ether, and an overhead fraction comprising methanol, linear olefins, linear alkanes and iso-alkanes;

(c) passing at least a portion of said overhead fraction to a distillation zone maintained under conditions sufficient to effectively separate linear olefins from said portion of said overhead fraction, and withdrawing i) a higher boiling linear olefin-rich bottoms fraction and ii) a lower boiling iso-alkane rich overhead fraction further comprising minor amounts of alkanol and water;

(d) passing at least a portion of said linear olefins-rich higher boiling bottoms fraction to an isomerization zone for the skeletal isomerization of linear olefins to iso-olefins and contacting said portion with a catalyst comprising a siliceous acidic zeolite in the hydrogen form, having Brönsted acid activity, capable of sorbing 10 to 40 mg 3-methylpentane at 90° C., 90 torr, per g dry zeolite, at skeletal isomerization conditions; and (e) withdrawing an isomerization zone effluent stream comprising iso-olefins from said isomerization zone and passing at least a portion of said isomerization zone effluent to at least one of said etherification reaction zones.

More particularly, the present invention relates to a continuous integrated process for producing tertiary alkyl methyl ether (TAME) from methanol and FCC C5 hydrocarbon feedstock containing linear pentenes, iso-pentenes, linear pentanes and iso-pentanes comprising:

(a) contacting said methanol and said hydrocarbon feedstock with acid etherification catalyst under iso-olefin etherification conditions in a first etherification reaction zone;

(b) passing at least a portion of the effluent from said first etherification reaction zone which effluent comprises tert-amyl methyl ether (TAME), methanol, iso-pentenes, linear pentenes, linear pentanes and iso-pentanes to a second etherification reaction zone which is a reactive distillation zone and withdrawing from said zone a high boiling fraction comprising said ether, and an overhead fraction comprising methanol, linear pentenes, linear pentanes and iso-pentanes;

(c) passing at least a portion of said overhead fraction to a distillation zone maintained under conditions sufficient to effectively separate linear pentenes from said portion of said overhead fraction, and withdrawing i) a higher boiling linear pentenes-rich bottoms fraction substantially free of methanol and water and ii) a lower boiling iso-pentane-rich overhead fraction further comprising minor amounts of methanol and water;

(d) passing at least a portion of said linear pentenes-rich higher boiling bottoms fraction to an isomerization zone for the skeletal isomerization of linear pentenes to iso-pentenes and contacting said portion with a catalyst comprising a siliceous acidic zeolite in the hydrogen form, having Brönsted acid activity, capable of sorbing 10 to 40 mg 3-methylpentane at 90° C., 90 torr, per g dry zeolite, at skeletal isomerization conditions; and (e) withdrawing an isomerization zone effluent stream comprising iso-pentenes from said isomerization zone and passing at least a portion of said isomerization zone effluent to at least one of said etherification reaction zones.

Although the iso-olefin rich isomerization zone effluent can be passed to the first etherification reaction zone, it is advantageous to direct this effluent to a subsequent etherification zone in order to facilitate an excess of alkanol in the first reaction zone for maximizing iso-olefin conversion to ether. Iso-olefins can be directly introduced to the second or subsequent etherification reaction zone in order to react with unreacted alkanols from the first reaction zone.

DETAILED DESCRIPTION OF THE INVENTION

The present invention provides a process which utilizes both linear olefins and iso-olefins in a $C_4$, $C_5$, $C_4+$ or $C_5+$ hydrocarbon feedstream for the production of lower alkyl tert-butyl ether by alkanol etherification. Etherification of linear olefins is accomplished by isomerization using a zeolite catalyzed isomerization process to produce iso-olefins which are then etherified to produce alkyl tert-butyl ethers.

Linear olefins for the isomerization reactor may be derived from a fresh feedstream, preferably comprising n-pentenes, or from the effluent of a liquid phase iso-olefin etherification reactor which employs alkanol and $C_4$, $C_5$, $C_4+$ or $C_5+$ hydrocarbon feedstock.

The feedstock to the etherification step of the present invention includes lower alkanol and $C_4+$ hydrocarbons rich in iso-olefins. Typical hydrocarbon feedstock materials for etherification reactions according to the present invention include olefinic streams, such as cracking process light hydrocarbons. Where the etherification process is one for the production of butyl ethers, the typical feedstream will consist of a mixture of C4 isomers comprising isobutane, isobutene, normal butane, 1-butene and 2-butene. Where amyl ethers are prepared, the feedstream will include 3-methyl-1-butene, isopentane, 1-pentene, 2-methyl-1-butene, normal pentane, trans-2-pentene, cis-2-pentene and 2-methyl-2-butene in a typical distribution of isomers. Because alkanes are not effectively reacted by the combined etherification/isomerization process of the present invention, these components increase the amount of material that passes through the process and must be removed to prevent high concentrations of unreactive material cycling through the reactors. This can be achieved efficiently by distilling the overhead effluent from the etherification reaction zones of alkanes, e.g. iso- and n-pentanes, after the final etherification reaction zone. Additionally, linear alkanes, e.g. n-pentane, may be removed by simply purging the overhead effluent from the final etherification reaction zone and before the distillation column used to separate linear olefins from iso-alkane, e.g., isopentane-containing streams.

The liquid phase reaction of methanol with isobutylene and isoamylenes at moderate conditions with a resin catalyst is known technology, as provided by R. W. Reynolds, et al., *The Oil and Gas Journal*, Jun. 16, 1975, and S. Pecci and T. Floris, *Hydrocarbon Processing*, December 1977. An article entitled "MTBE and TAME—A Good Octane Boosting Combo," by J. D. Chase, et al., *The Oil and Gas Journal*, Apr. 9, 1979, pages 149–152, discusses the technology. Preferred catalysts are polymeric sulfonic acid exchange resin such as Amberlyst 15 and zeolites such as zeolite Beta and ZSM-5. The acid resin catalysts are effective catalysts at temperatures below 90° C. At higher temperatures the resin catalyst is unstable.

In the etherification process it is known that alkanol and iso-olefins may be reacted in equimolar quantities or either reactant may be in molar excess to influence the complete conversion of the other reactant. Because etherification is an incomplete reaction the etherification effluent comprises unreacted alkanol and unreacted hydrocarbons. In a variation of the plural stage etherification zone process of the present invention, it is advantageous to operate with a molar excess of alkanol in the first stage in order to increase conversion of the iso-olefins in the feed to ether due to favorable equilibrium conditions. Excess alkanol in the first etherification reaction zone effluent passes to the second etherification zone where it reacts with iso-olefins, e.g., from the isomerization zone effluent. This provides an improvement over present methods which avoid higher alkanol to iso-olefin ratios in order to minimize operating costs associated with alkanol, e.g., methanol, recovery, which is necessary to avoid damaging the isomerization catalyst.

In the present invention, an alkanol to iso-olefin ratio of greater than 1 is maintained in said first etherification zone and an alkanol to iso-olefin ratio lower than in said first etherification zone is maintained in said second etherification zone. Preferably, an alkanol to iso-olefin ratio lower than that of said first etherification zone is maintained in the second etherification zone such that the amount of alkanol in the second etherification zone does not exceed the azeotropic limit for the overhead fraction from the second etherification reaction zone which contains alkanol, linear olefins, linear alkanes and iso-alkanes. In the first etherification reaction zone of the present invention, the molar ratio of alkanol to iso-olefin, such as methanol to iso-amylene, can be between 1.1 and 2.5, preferably between 1.1 and 2.0. The second etherification reaction zone has a molar ratio of alkanol to iso-olefin, such as methanol to iso-amylene, which is lower than the first etherification zone, e.g, between 0.9, and 1.2, preferably between 1.0 and 1.1.

Iso-olefins or isoalkenes in this invention are those having the formula $R_2C=CH_2$ or $R_2C=CHR$, particularly $C_4$–$C_7$ iso-olefins. Alkanols which may be used in the present invention include methanol, ethanol, 1-propanol, isopropanol, 1-butanol and 2-butanol. The term lower alkyl refers to $C_1$–$C_4$ alkyl including methyl, ethyl, n-propyl, isopropyl, n-butyl, sec-butyl, isobutyl and tert-butyl.

Suitable alkanol feeds to the process include lower aliphatic $C_1$–$C_4$ primary or secondary alcohols, but preferably methanol. Ethanol, although used less commonly, is also a commonly available alcohol for the etherification process.

The isomerization zone of the present invention is maintained at a temperature of about 200° C. to 600° C., preferably 250° C. to 500° C., an olefin partial pressure between about 20 kPa and 1000 kPa, preferably between about 100 and 500 kPa and an olefin WHSV between about 1.0 and 500, preferably between about 5 and 100.

Catalyst

The preferred catalysts, exemplified by ZSM-22, ZSM-23, and ZSM-35, are members of a unique class of zeolites. They have channels described by 10-membered rings of T (=Si or Al) or oxygen atoms, i.e., they are intermediate pore zeolites, distinct from small pore 8-ring or large pore 12-ring zeolites. They differ, however, from other intermediate pore 10-ring zeolites, such as ZSM-5, ZSM-11, ZSM-57 or stilbite, in having a smaller 10-ring channel. If the crystal structure (and hence pore system) is known, a convenient measure of the channel cross-section is given by the product of the dimensions (in angstrom units) of the two major axes of the pores. These dimensions are listed in the "Atlas of Zeolite Structure Types" by W. M. Meier and D. H. Olson, Butterworths, publisher, Second Edition, 1987. The values of this product, termed the Pore Size Index, are listed in Table A.

TABLE A

Pore Size Index

| Type | Largest Ring Size | Zeolite | Axes of Largest Channel, A | Pore Size Index |
|---|---|---|---|---|
| 1 | 8 | Chabazite | 3.8 × 3.8 | 14.4 |
|  |  | Erionite | 3.6 × 5.1 | 18.4 |
|  |  | Linde A | 4.1 × 4.1 | 16.8 |
| 2 | 10 | ZSM-22 | 4.4 × 5.5 | 24.2 |
|  |  | ZSM-23 | 4.5 × 5.2 | 23.4 |
|  |  | ZSM-35 | 4.2 × 5.4 | 22.7 |
|  |  | ALPO-11 | 3.9 × 6.3 | 24.6 |
| 3 | 10 | ZSM-5 | 5.3 × 5.6 | 29.1 |
|  |  | ZSM-11 | 5.3 × 5.4 | 28.6 |
|  |  | Stilbite | 4.9 × 6.1 | 29.9 |
|  |  | ZSM-57 (10) | 5.1 × 5.8 | 29.6 |
| 4 | 12 | ZSM-12 | 5.5 × 5.9 | 32.4 |
|  |  | Mordenite | 6.5 × 7.0 | 45.5 |
|  |  | Beta (C-56) | 6.2 × 7.7 | 47.7 |
|  |  | Linde-L | 7.1 × 7.1 | 50.4 |
|  |  | Mazzite (ZSM-4) | 7.4 × 7.4 | 54.8 |
|  |  | ALPO$_4$-5 | 7.3 × 7.3 | 53.3 |

It can be seen that small pore, eight-ring zeolites have a Pore Size Index below about 20, the intermediate pore, 10-ring zeolites of about 20–31, and large pore, 12-ring zeolites above about 31. It is also apparent, that the 10-ring zeolites are grouped in two distinct classes; Type 2 with a Pore Size Index between about 22.7 and 24.6, and more broadly between about 20 and 26, and Type 3 with a Pore Size Index between 28.6 and 29.9, or more broadly, between about 28 and 31.

The zeolites useful for this invention are those of Type 2 with a Pore Size Index of 20–26.

The Type 2 zeolites are distinguished from the other types by their sorption characteristics towards 3-methylpentane. Representative equilibrium sorption data and experimental conditions are listed in Table B.

Type 2 zeolites sorb in their intracrystalline voids at least about 10 mg and less than about 40 mg of 3-methylpentane at 90° C., 90 torr 3-methylpentane, per gram dry zeolite in the hydrogen form. In contrast, Type 3 zeolites sorb greater than 40 mg 3-methylpentane under the conditions specified.

The equilibrium sorption are obtained most conveniently in a thermogravimetric balance by passing a stream of inert gas such as helium containing the hydrocarbon with the indicated partial pressure over the dried zeolite sample held at 90° C. for a time sufficient to obtain a constant weight.

Samples containing cations such as sodium or aluminum ions can be converted to the hydrogen form by well-known methods such as exchange at temperatures between 25° and 100° C. with dilute mineral acids, or with hot ammonium chloride solutions followed by calcination. For mixtures of zeolites with amorphous material or for poorly crystallized samples, the sorption values apply only to the crystalline portion.

This method of characterizing the Type 2 zeolites has the advantage that it can be applied to new zeolites whose crystal structure has not yet been determined.

TABLE B

Equilibrium Sorption Data of Medium Pore Zeolites
Amount sorbed, mg per g zeolite

| Type | Zeolite | 3-Methylpentane[a] |
|---|---|---|
| 2 | ZSM-22 | 20 |
|  | ZSM-23 | 25 |
|  | ZSM-35 | 25 |
| 3 | ZSM-5 | 61 |
|  | ZSM-12 | 58 |
|  | ZSM-57 | 70 |
|  | MCM-22 | 79 | a) at 90° C., 90 torr 3-methylpentane

ZSM-22 is more particularly described in U.S. Pat. No. 4,556,477, the entire contents of which are incorporated herein by reference. ZSM-22 and its preparation in microcrystalline form using ethylpyridinium as directing agent is described in U.S. Pat. No. 4,481,177 to Valyocsik, the entire contents of which are incorporated herein by reference. For purposes of the present invention, ZSM-22 is considered to include its isotypes, e.g., Theta-1, Gallo-Theta-1, NU-10, ISI-1, and KZ-2.

ZSM-23 is more particularly described in U.S. Pat. No. 4,076,842, the entire contents of which are incorporated herein by reference. For purposes of the present invention, ZSM-23 is considered to include its isotypes, e.g., EU-13, ISI-4, and KZ-1.

ZSM-35 is more particularly described in U.S. Pat. No. 4,016,245, the entire contents of which are incorporated herein by reference. For purposes of the present invention, ZSM-35 is considered to include its isotypes, e.g., ferrierite, FU-9, ISI-6, NU-23, and Sr-D. An example of a piperidine-derived ferrierite is more particularly described in U.S. Pat. No. 4,343,692, the entire contents of which are incorporated herein by reference. Other synthetic ferrierite preparations are described in U.S. Pat. Nos. 3,933,974; 3,966,883; 4,000,248; 4,017,590; and 4,251,499, the entire contents of all being incorporated herein by reference. Further descriptions of ferrierite are found in Bibby et al, "Composition and Catalytic Properties of Synthetic Ferrierite," Journal of Catalysis, 35, pages 256–272 (1974).

The zeolite catalyst used is preferably at least partly in the hydrogen form, e.g., HZSM-22, HZSM-23, or HZSM-35. Other metals or cations thereof, e.g. rare earth cations, may also be present. When the zeolites are prepared in the presence of organic cations, they may be quite inactive possibly because the intracrystalline free space is occupied by the organic cations from the forming solution. The zeolite may be activated by heating in an inert or oxidative atmosphere to remove the organic cations, e.g. by heating at over 500° C. for 1 hour or more. The hydrogen form can then be obtained by base exchange with ammonium salts followed by calcination, e.g., at 500° C. in air. Acid treatment may result in dealumination and is therefore not typically practiced. Other cations, e.g. metal cations, can be introduced by conventional base exchange or impregnation techniques.

The zeolite may be incorporated in another material usually referred to as a matrix or binder. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

Of all the foregoing materials, silica may be preferred as the matrix material owing to its relative inertness for catalytic cracking reactions which are preferably minimized in the instant processes. The relative proportions of finely divided zeolite and inorganic oxide gel matrix vary widely with the zeolite content ranging from about 1 to about 90 percent by weight and more usually in the range of about 30 to about 80 percent by weight of the composite.

The regeneration of spent zeolite catalyst used in the oligomerization reaction is carried out oxidatively or hydrogenatively employing procedures known in the art.

In order to obtain desired olefin oligomerization activity/selectivity, the zeolite, preferably in the hydrogen form, should have an alpha value between about 5 and 400, preferably between about 10 and 100 when used in the catalyst of the present invention. Alpha value, or alpha number, of a zeolite is a measure of zeolite acidic functionality and is more fully described together with details of its measurement in U.S. Pat. No. 4,016,218, *J. Catalysis*, 6, pp. 278–287 (1966) and *J. Catalysis*, 61, pp. 390–396 (1980). The experimental conditions cited in the latter reference are used for characterizing the catalysts described herein.

Figure 1:
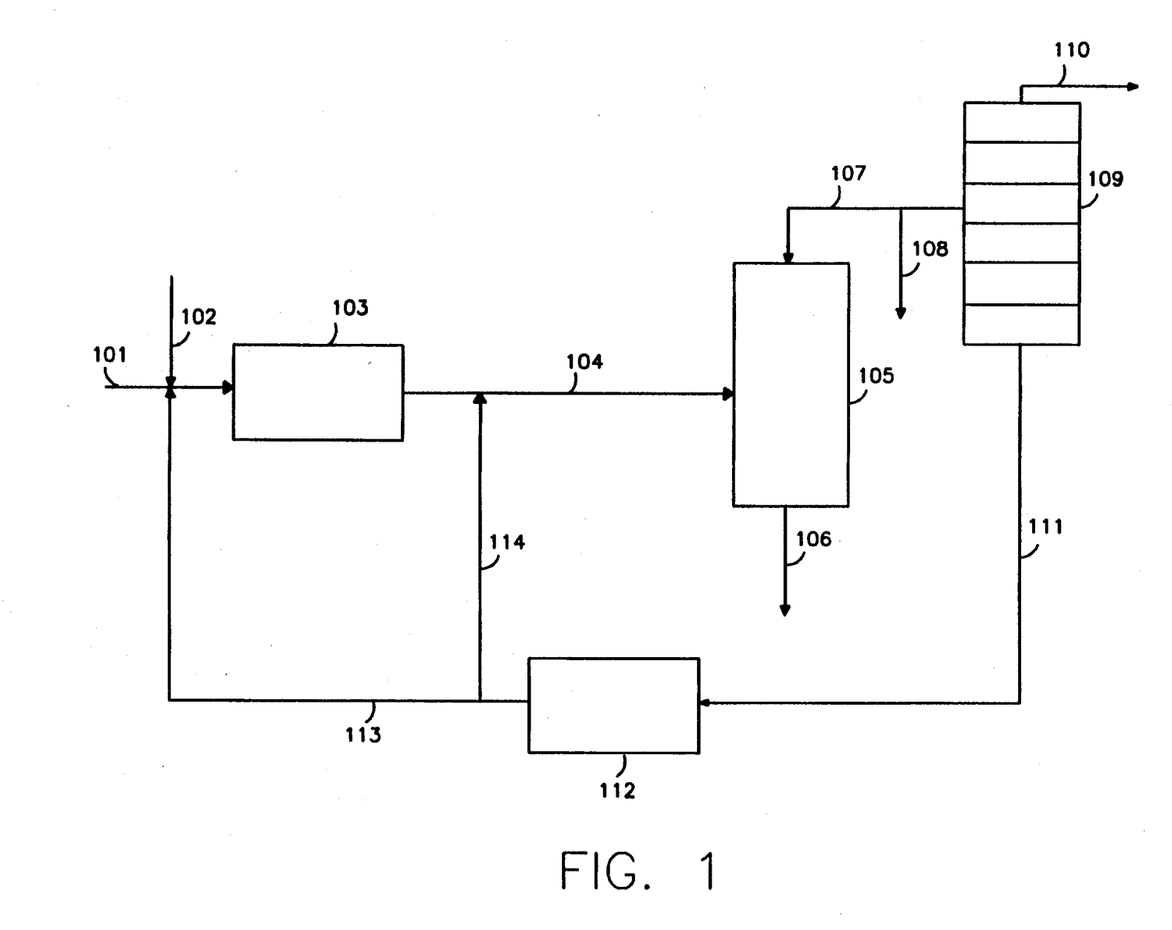
FIG. 1 is a schematic process flow diagram of the present invention illustrating the integration of skeletal isomerization with plural stage etherification combined with a distillation column maintained at conditions suited to separating overhead from the final etherification stage into a linear olefin-rich bottoms fraction for isomerization and an iso-alkane-containing overhead suited to incorporation in the gasoline pool of a refinery.

Referring to FIG. 1, a simplified process flow diagram for a preferred embodiment of the invention provides a continuous process for the isomerization of linear olefins to iso-olefins followed by etherification of iso-olefins with alkanol to produce substantially higher yields of alkyl tertiary alkyl ethers based on total olefins processed. Fresh FCC C5 feed 101 containing linear pentenes, isopentene, n-pentanes, isopentane and methanol feed 102 are introduced into a first etherification reaction zone 103 containing etherification catalyst which is maintained under etherification conditions. The first etherification reaction zone effluent 104 which contains TAME, unreacted methanol, pentanes, linear pentenes and iso-pentenes is directed to a second stage etherification reaction zone 105 (reactive distillation zone) which further etherifies the effluent 104 and from which a TAME-containing ether bottoms product 106 is collected. Overhead 107 from the reactive distillation zone comprises linear pentanes, isopentane, linear pentenes and minor amounts of methanol and water. Since the combined etherification and skeletal olefin isomerization process of the present invention does not react alkanes to any significant degree, these components increase the amount of material that passes through the process and can be removed beyond that achieved by distillation by optionally purging through line 108 as necessary, e.g., to reduce linear pentane content. The purged or unpurged feedstream 107 is passed to a distillation column 109 which is maintained at conditions sufficient to effectively separate an overhead 110 largely containing isopentane and minor amounts of methanol and water from a linear pentenes-containing bottoms 111. The overhead 110 may be further treated to remove methanol and water, however, it can be added to the refinery gasoline pool without further modification, given the minor amounts of methanol and water impurities present. The n-pentenes containing bottoms 111 are cycled to the skeletal isomerization reaction zone 112 wherein linear pentenes are converted to an isopentene-rich effluent 113. Effluent 113 can be directed to either or both of the etherification reaction zones via lines 113 and 114. Methanol to isopentene ratios in the respective etherification reaction zones can be modified by such directing of isomerization effluent to the respective etherification zones.

Figure 2:
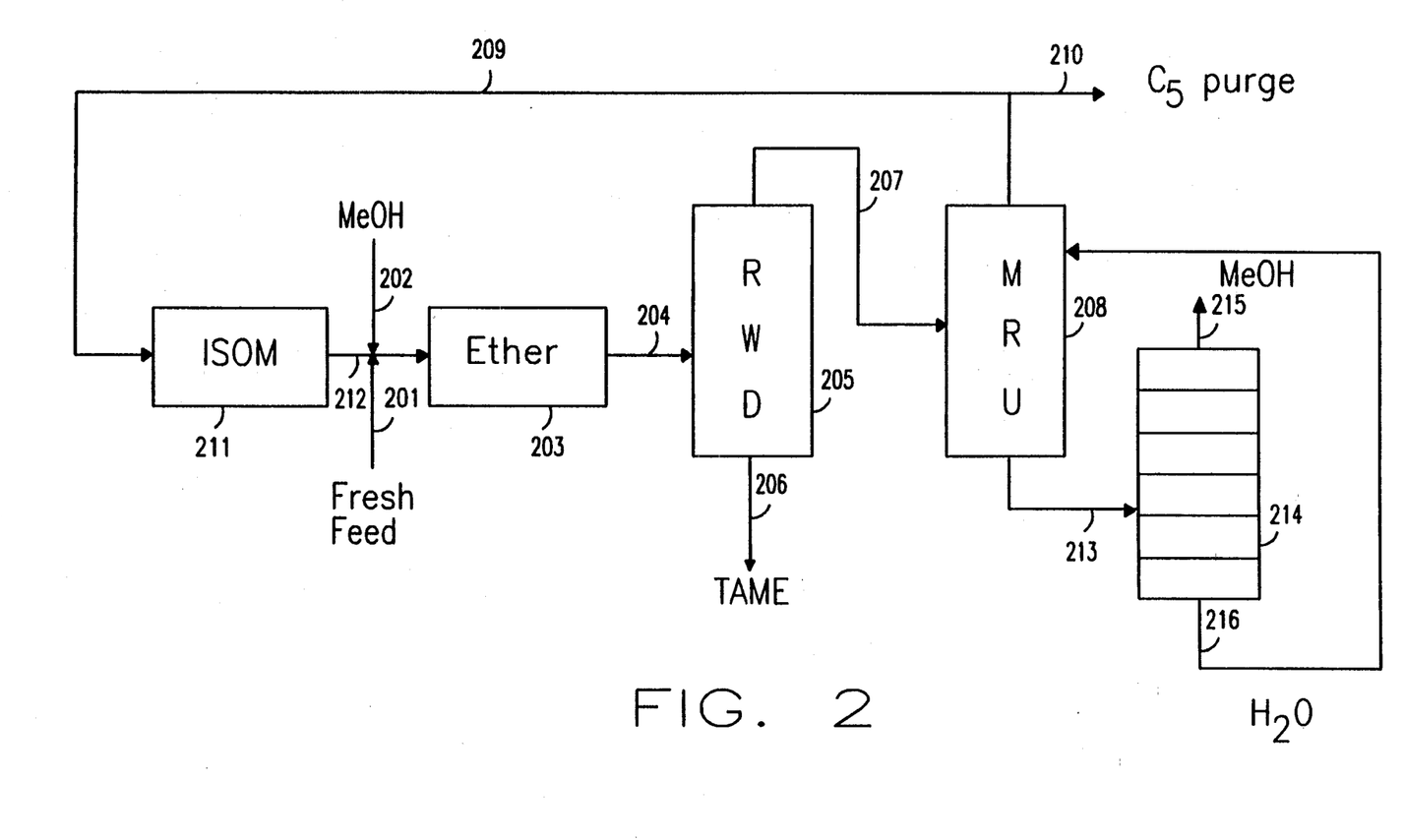
FIG. 2 is a schematic process flow diagram of a conventional process employing integration of skeletal isomerization with plural stage etherification combined with an alkanol recovery unit employing water extraction and a subsequent distillation column maintained at conditions suited to separating alkanol from water.

Referring to FIG. 2, a simplified process flow diagram is provided for a continuous process for the isomerization of linear olefins to iso-olefins followed by etherification of iso-olefins with alkanol to produce alkyl tertiary alkyl ethers which does not employ a concentrated recycle stream treated to remove iso-pentanes. Fresh FCC C5 feed 201 containing linear pentenes, isopentene, n-pentanes, isopentane and methanol feed 202 are introduced into a first etherification reaction zone 203 containing etherification catalyst which is maintained under etherification conditions. The first etherification reaction zone effluent 204 which contains TAME, unreacted methanol, pentanes, linear pentenes and iso-pentenes is directed to a second stage etherification reaction zone 205 (reactive distillation zone) which further etherifies the effluent 204 and from which a TAME-containing ether bottoms product 206 is collected. Overhead 207 from the reactive distillation zone comprising linear pentanes, isopentane, linear pentenes, and minor amounts of methanol and water, is passed to a methanol recovery unit (MRU) 208 where water is used to extract methanol. The overhead 209 from the methanol recovery unit comprises linear pentenes and pentanes, the latter being purged through line 210. The linear pentene-containing feed is passed to skeletal isomerization unit 211 to provide an isopentene enriched feed 212 which is passed to the first etherification reaction zone 203. The bottoms 213 from the methanol recovery unit containing methanol and water is passed to a distillation column 214 which provides a methanol overhead 215 and water-containing bottoms 216 which are cycled to the methanol recovery unit 208.

EXAMPLES 1, 1a and 1b

ZSM-35-containing catalysts described in Table 1 below were prepared as follows:

Example 1

Preparation of ZSM-35

1.18 parts of aluminum sulfate (17.2% $Al_2O_3$) were added to a solution containing 9.42 parts $H_2O$ and 1.38 parts of 50% NaOH solution in an autoclave. 0.03 parts of ZSM-35 seeds and 3.20 parts of Hi-Sil precipitated silica were added with agitation, followed by 1.0 part of pyrrolidine.

The reaction mixture had the following composition, in mole ratios:

| | |
|---|---|
| $SiO_2/Al_2O_3$ | 21.5 |
| $OH^-/SiO_2$ | 0.11 |
| $H_2O/Al_2O_3$ | 13.5 |
| $R/Al_2O_3$ | 6.45 |

Example 1a

Preparation of Silica-Bound HZSM-35

A catalyst was prepared by dry mixing the as-synthesized ZSM-35 of Example 1 with precipitated silica. Colloidal silica, in proportion to give 65% ZSM-35/35% silica after calcination, and water were added to the dry mix to obtain an extrudable mull. The mull was extruded to 1/16 inch (1.6 mm) diameter, dried at 120° C., calcined in nitrogen for three hours at 538° C., and then in air for 6 hours at 538° C. The extrudate was exchanged two times with 1N $NH_4NO_3$ solution at room temperature, rinsed with deionized water, dried at 120° C. and calcined in nitrogen for 3 hours at 538° C.

Example 1b

Preparation of silica-Bound HZSM-35

A catalyst was prepared by dry mixing the as-synthesized ZSM-35 of Example 1 with precipitated silica. Colloidal silica, in proportion to give 65% ZSM-35/35% silica after calcination, and water were added to the dry mix to obtain an extrudable mull. The mull was extruded to 1/16 inch (1.6 mm) diameter, dried at 120° C., and then calcined in nitrogen for three hours at 538° C. The extrudate was exchanged two times with 1N $NH_4NO_3$ solution at room temperature, rinsed with deionized water, dried at 120° C. and calcined in air for 9 hours at 538° C.

The resulting catalysts were used to process the pentene-containing feeds of Table 2 below, resulting in up to 80% conversion of n-pentene to tertiary pentenes at selectivities as high as 99%.

TABLE 1

ZSM-35 CATALYST PROPERTIES

| Properties | Example 1a | Example 1b |
|---|---|---|
| Catalyst alpha[a] | 106 | 93 |
| Particle density, g/cc | 0.94 | 0.86 |
| Surface area, $m^2/g$ | 269 | 287 |
| Pore volume, cc/g | 0.63 | 0.72 |
| Avg. Pore diameter, Å | 93 | 99 |
| Sodium, ppm | 130 | 160 |

[a]Catalyst contains 65 wt % zeolite in silica binder

TABLE 2

| Reaction Conditions | Example 1a | Example 1b |
|---|---|---|
| Temperature, °F. | 700 | 475 |
| Fresh Feed WHSV | 4.8 | 5.0 |
| Pressure, psig | 85 | 116 |

TABLE 2-continued

| Composition, wt % | Feed | Product | Feed | Product |
|---|---|---|---|---|
| $C_3-$ | 0.0 | 0.2 | 0.0 | 0.0 |
| $n-C_4=$ | 0.1 | 0.1 | 0.0 | 0.0 |
| $iso-C_4=$ | 0.0 | 0.1 | 0.0 | <0.1 |
| $n-C_4$ | 0.0 | 0.0 | 0.0 | 0.0 |
| $iso-C_4$ | 0.0 | 0.0 | 0.0 | 0.0 |
| $3M1C_5=$ | 0.0 | 1.0 | <0.1 | 0.6 |
| $1-C_5=$ | 33.4 | 1.4 | 12.3 | 0.7 |
| $t2C_5=$ | 0.0 | 5.2 | 14.4 | 3.6 |
| $c2C_5$ | 0.0 | 2.6 | 5.3 | 1.6 |
| $2M1C_4=$ | 1.4 | 7.0 | 0.4 | 5.7 |
| $2M2C_4$ | 0.0 | 17.3 | 0.5 | 20.4 |
| $C_5$ dienes | 0.2 | 0.1 | <0.05 | 0.05 |
| $n-C_5$ | 0.5 | 0.5 | 7.2 | 7.3 |
| $iso-C_5$ | 64.3 | 64.4 | 59.9 | 60.0 |
| $C_6+$ | 0.1 | 0.1 | 0.0 | <0.1 |
| | 100 | 100 | 100 | 100 |

Example 2 (Comparative)

Figure 3:
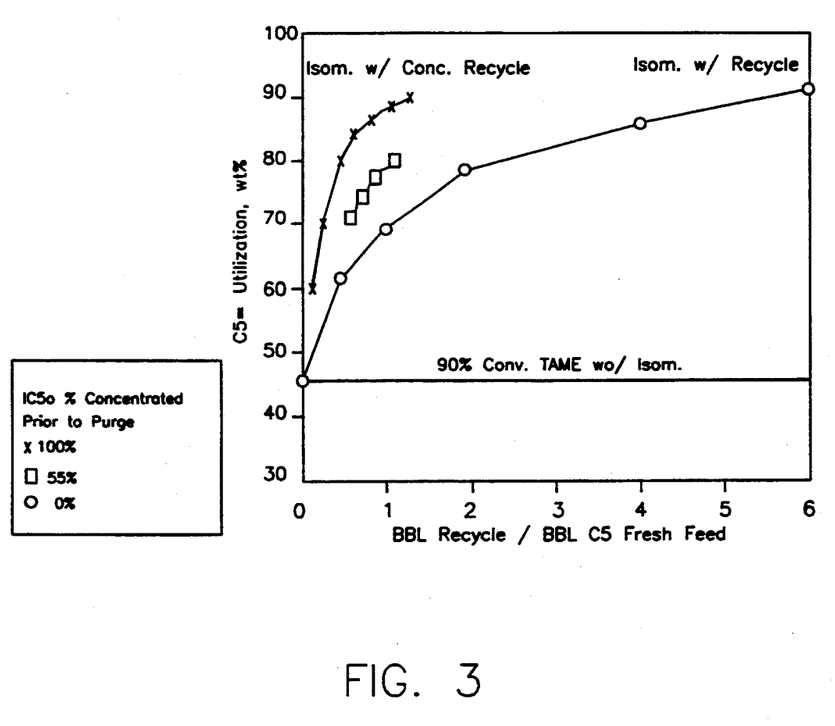
FIG. 3 is a graph depicting C5 olefin utilization (wt %) over increasing recycle/fresh feed (vol/vol) ratios for etherification without isomerization, integrated etherification and isomerization with recycle of isopentane containing feed, and integrated etherification and isomerization with recycle of isopentane depleted feed (concentrated recycle).
Figure 4:
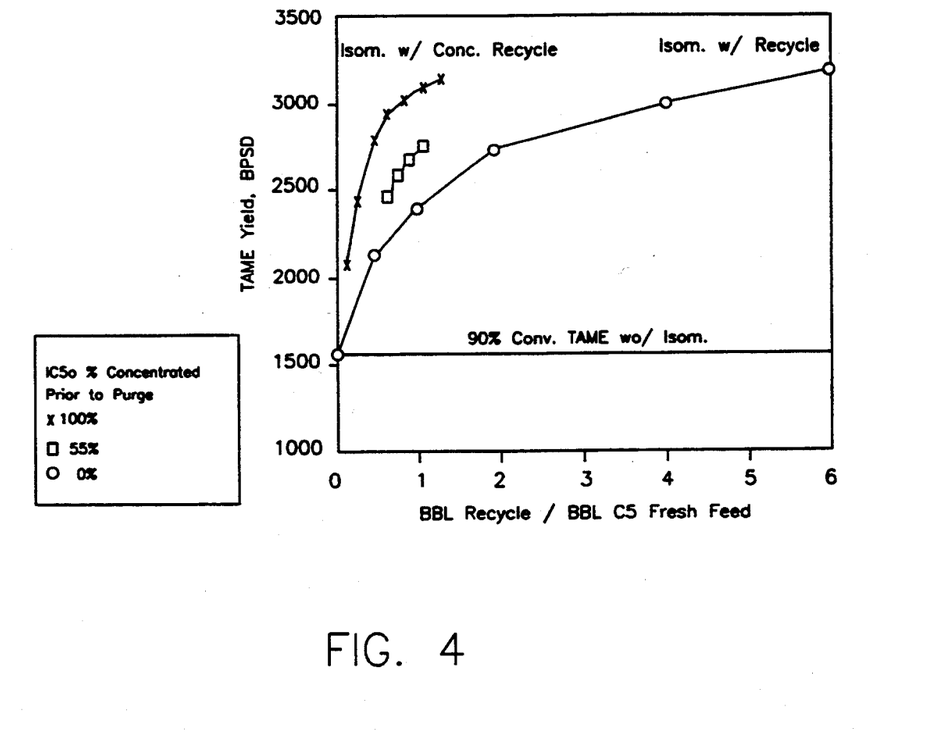
FIG. 4 is a graph depicting TAME yield (BPSD) over increasing recycle/fresh feed (vol/vol) ratios for etherification without isomerization, integrated etherification and isomerization with recycle of isopentane containing feed, and integrated etherification and isomerization with recycle of isopentane depleted feed (concentrated recycle).

Simulations were performed to calculate overall TAME yield using the refinery FCC C5 feed listed in Table 3 for the process of FIG. 2 (above) using olefin isomerization yields from Example 1a and literature reports for 90% tertiary pentene conversion in two-stage TAME processes as reported in *Hydrocarbon Processing*, March 1993, page 194, and by J. L. DeGramo et al. *Chemical Engineering Progress*, March 1992, page 43. Simulations carried out at recycle ratios (vol recycle/vol C5 fresh feed) ranging from 0 to 6 (vol recycle/vol C5 fresh feed) showed that increasing recycle ratios increases C5= utilization (FIG. 3) and TAME yield (FIG. 4). However, these benefits are realized at the expense of a nearly seven-fold increase in etherification reactor size as shown in Table 4 below.

TABLE 3

Refinery FCC C5 FEED COMPOSITION

| Composition | BPSD | (vol. %): |
|---|---|---|
| n-pentene | 737 | 7.0 |
| i-pentene | 7127 | 67.4 |
| 1-pentene | 272 | 2.6 |
| c-2-pentene | 338 | 3.2 |
| t-2-pentene | 619 | 5.8 |
| 3-methyl-1-butene | 82 | 0.8 |
| 2-methyl-1-butene | 410 | 3.9 |
| 2-methyl-2-butene | 983 | 9.3 |
| Total | 10,568 | 100.0 |

*Barrel per stream day (BPSD)

TABLE 4

Effect of Recycle on Reactor Size

| Recycle Ratio | 0 | 0.5 | 1.0 | 2.0 | 4.0 | 6.0 |
|---|---|---|---|---|---|---|
| Tame, BPSD | 1615 | 2108 | 2401 | 2722 | 2996 | 3115 |
| C5= Utilization, wt % | 46.4 | 61.0 | 69.7 | 79.3 | 87.4 | 91.0 |
| Isom. Reactor | | | | | | |
| FF Isom, MM lb/day | 0 | 1.16 | 2.31 | 4.62 | 9.22 | 13.8 |
| Isom Feed nC5=, wt % | — | 10.9 | 8.7 | 6.1 | 3.8 | 2.7 |
| Ether Reactor | | | | | | |
| Ether Feed, MM lb./day | 2.34 | 3.50 | 4.65 | 6.96 | 11.56 | 16.16 |
| Ether Feed tert-C5=, wt % | 13.8 | 12.1 | 10.3 | 7.8 | 5.2 | 3.9 |

Example 3

Simulations were performed to calculate overall TAME yield using the refinery FCC C5 feed listed in Table 3 for the process of the present invention (FIG. 1 above) wherein the recycle from the isomerization reactor is directed to the first etherification reaction zone.

The simulation employs olefin isomerization yields from Example 1a and the above-noted literature data for 90% tertiary pentene conversion in two-stage TAME processes. Simulations carried out at recycle ratios (vol recycle/vol C5 fresh feed) ranging up to about 1.3 (vol recycle/vol C5 fresh feed) showed that relatively low recycle ratios achieve impressive C5= utilization (FIG. 3) and TAME yield (FIG. 4) for processes recovering 100% and 55% of feed isopentane in the distillation tower overhead. The invention reduces etherification and isomerization reactor sizes as shown in Table 5 below (for the 55% isopentane recovery case) by processing a more concentrated olefin stream. Furthermore, the use of distillation to concentrate the recycle stream provides for removal of methanol without water washing. This eliminates contact of the olefin isomerization feed with water, a potential agent for hydrothermal damage of the zeolite isomerization catalyst.

TABLE 5

Effect of Concentrated Recycle

| | No Recycle | Concentrated Recycle | Bulk Recycle |
|---|---|---|---|
| Recycle Ratio | 0 | 1.0 | 2.0 |
| Tame, BPSD | 1615 | 2735 | 2722 |
| C5= utilization, wt % | 46.4 | 79.6 | 79.3 |
| Isom Reactor | | | |
| FF Isom, xMM lb/day | — | 2.2 | 4.6 |
| Isom feed nC5= conc., wt % | — | 12.9 | 6.1 |
| Ether Reactor | | | |
| Ether Feed, MM lb/day | 2.3 | 4.6 | 7.0 |
| Ether feed tert-C5= conc., wt % | 13.8 | 12.0 | 7.8 |
| Deisopentanizer | | | |
| Stages | — | 17 | — |
| condenser-duty, MMBTU/hr | — | 25.5 | — |
| reboiler-duty, MMBTU/hr | — | 34.1 | — |
| Methanol Recovery Unit | no | no | yes |
| Isom feed, | | | |
| MeOH, ppm | — | <10 | 25-100 |
| H2O, ppm | — | <50 | >200 |

Example 4

Figure 5:
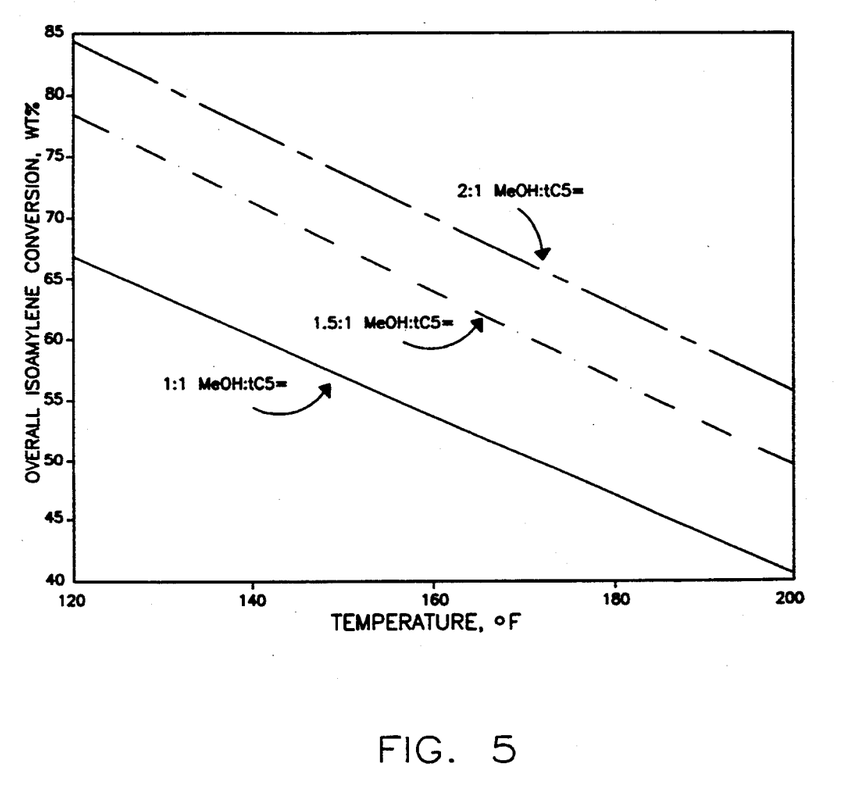
FIG. 5 is a graph depicting overall isoamylene conversion (wt %) with temperature at methanol to iso-amylene molar ratios of 1:1, 1.5:1 and 2:1.

Simulations using a high methanol to tertiary-olefin molar ratio (1:1) in the first etherification reactor were performed to calculate overall TAME yield using the C5 feed listed in Table 6 below for the process of the present invention (FIG. 1 above) wherein the recycle from the isomerization reactor is directed downstream of the first etherification reaction zone (to the second etherification reaction zone). Use of a higher methanol to tertiary-olefin molar ratio (>1:1) provides higher conversion of tertiary olefins in the fresh feed to TAME as shown in FIG. 5. At a reaction temperature of 140° F., increasing the MeOH to tertiary-C5= ratio from 1:1 to 1.5:1 in the first etherification reactor increases tertiary-C5= conversion from 60 to 72 wt %. Unconverted excess MeOH from the first etherification zone is reacted with tertiary olefins from the isomerization zone in the second etherification zone such that the amount of methanol in the reactive distillation zone (second etherification zone) does not exceed the azeotropic limit for the overhead stream. In conventional TAME processes, increasing the MeOH: tertiary-C5= to 1.5:1 would result in methanol in the ether product whereas the present invention effectively reacts methanol to provide an effectively methanol-free product TAME.

TABLE 6

Iso-Amylene/Methanol/TAME Equilibrium
150 psig - FCC C5 Feed (wt %):

| | |
|---|---|
| 4.5 | 2m1C4= |
| 8.6 | 2m2C4= |
| 17.2 | Other C5= |
| 69.8 | C5 Paraffins |

While the instant invention has been described by specific examples and embodiments, there is no intent to limit the inventive concept except as set forth in the following claims.

What is claimed is:

1. A continuous integrated process for producing alkyl tertiary alkyl ether from alkanol and hydrocarbon feedstock containing linear olefins, iso-olefins, linear alkanes and iso-alkanes comprising:
   (a) contacting said alkanol and said hydrocarbon feedstock with acid etherification catalyst under iso-olefin etherification conditions in a first etherification reaction zone;
   (b) passing at least a portion of the effluent from said first etherification reaction zone which effluent comprises ether, alkanol, iso-olefins, linear olefins, linear alkanes and iso-alkanes to a second etherification reaction zone which is a reactive distillation zone and withdrawing from said zone a high boiling fraction comprising said ether, and an overhead fraction comprising alkanol, linear olefins, linear alkanes and iso-alkanes, which is purged to reduce linear alkane content;
   (c) passing at least a portion of said overhead fraction to a distillation zone maintained under conditions sufficient to effectively separate linear olefins from said portion of said overhead fraction, and withdrawing i) a higher boiling linear olefin-rich bottoms fraction and ii) a lower boiling iso-alkane rich overhead fraction further comprising minor amounts of alkanol and water;
   (d) passing at least a portion of said linear olefins-rich higher boiling bottoms fraction to an isomerization zone for the skeletal isomerization of linear olefins to iso-olefins and contacting said portion with a catalyst comprising a siliceous acidic zeolite in the hydrogen form, having Brönsted acid activity, capable of sorbing 10 to 40 mg 3-methylpentane at 90° C., 90 torr, per g dry zeolite, at skeletal isomerization conditions; and
   (e) withdrawing an isomerization zone effluent stream comprising iso-olefins from said isomerization zone and passing at least a portion of said isomerization zone effluent to at least one of said etherification reaction zones.

2. The process of claim 1 wherein at least a portion of said lower boiling iso-alkane rich overhead fraction further comprising minor amounts of alkanol and water is passed to a refinery gasoline pool.

3. The process of claim 1 wherein said isomerization zone effluent is passed to said first etherification reaction zone.

4. The process of claim 1 wherein said isomerization zone effluent is passed to said second etherification reaction zone.

5. The process of claim 1 wherein an alkanol to iso-olefin ratio of greater than 1 is maintained in said first etherification zone and an alkanol to iso-olefin ratio lower than in said first etherification zone is maintained in said second etherification zone.

6. The process of claim 4 wherein an alkanol to iso-olefin ratio of greater than 1 is maintained in said first etherification zone and an alkanol to iso-olefin ratio lower than that of said first etherification zone is maintained in said second etherification zone such that the amount of alkanol in the second etherification zone does not exceed the azeotropic limit for the overhead fraction from said second etherification reaction zone comprising alkanol, linear olefins, linear alkanes and iso-alkanes.

7. The process of claim 1 wherein said hydrocarbon feedstock is FCC C4+ stream; said alkanol feedstock comprises $C_1$–$C_4$ alkanol; said isomerization zone is maintained at a temperature of about 200° C. to 600° C., an olefin partial pressure between about 20 kPa and 1000 kPa and WHSV between about 1.0 and 500; and said isomerization zone catalyst has the structure selected from the group consisting of ZSM-22, ZSM-23, and ZSM-35.

8. The process of claim 1 wherein said hydrocarbon feedstock is FCC C5 stream; said alkanol feedstock comprises methanol; said isomerization zone is maintained at a temperature of about 200° C. to 600° C., an olefin partial pressure between about 50 and 500 kPa and WHSV between about 1 and 20; and said isomerization zone catalyst has the structure of ZSM-35.

9. The process of claim 1 wherein said alkyl tertiary-alkyl ether is methyl tertiary butyl ether (MTBE).

10. The process of claim 1 wherein said alkyl tertiary-alkyl ether is tertiary amyl methyl ether (TAME).

11. The process of claim 1 wherein said etherification catalyst comprises acidic zeolite or sulfonated polyvinyl aromatic resins.

12. The process of claim 1 wherein said isomerization zone comprises a fixed catalyst bed, and including the step of oxidatively or hydrogenatively regenerating said catalyst.

13. A continuous integrated process for producing tertiary alkyl methyl ether (TAME) from methanol and FCC C5 hydrocarbon feedstock containing linear pentenes, iso-pentenes, linear pentanes and iso-pentanes comprising:
(a) contacting said methanol and said hydrocarbon feedstock with acid etherification catalyst under iso-olefin etherification conditions in a first etherification reaction zone;
(b) passing at least a portion of the effluent from said first etherification reaction zone which effluent comprises tert-amyl methyl ether (TAME), methanol, iso-pentenes, linear pentenes, linear pentanes and iso-pentanes to a second etherification reaction zone which is a reactive distillation zone and withdrawing from said zone a high boiling fraction comprising said ether, and an overhead fraction comprising methanol, linear pentenes, linear pentanes and iso-pentanes, which is purged to reduce linear alkane content;
(c) passing at least a portion of said overhead fraction to a distillation zone maintained under conditions sufficient to effectively separate linear pentenes from said portion of said overhead fraction, and withdrawing i) a higher boiling linear pentenes-rich bottoms fraction substantially free of methanol and water and ii) a lower boiling iso-pentane-rich overhead fraction further comprising minor amounts of methanol and water;
(d) passing at least a portion of said linear pentenes-rich higher boiling bottoms fraction to an isomerization zone for the skeletal isomerization of linear pentenes to iso-pentenes and contacting said portion with a catalyst comprising a siliceous acidic zeolite in the hydrogen form, having Brönsted acid activity, capable of sorbing 10 to 40 mg 3-methylpentane at 90° C., 90 torr, per g dry zeolite, at skeletal isomerization conditions; and
(e) withdrawing an isomerization zone effluent stream comprising iso-pentenes from said isomerization zone and passing at least a portion of said isomerization zone effluent to at least one of said etherification reaction zones.

14. The process of claim 13 wherein at least a portion of said lower boiling iso-pentane rich overhead fraction further comprising minor amounts of methanol and water is passed to a refinery gasoline pool.

15. The process of claim 13 wherein said isomerization zone effluent is passed to said second etherification reaction zone.

16. The process of claim 13 wherein a methanol to iso-pentene ratio of greater than 1 is maintained in said first etherification zone and a methanol to iso-pentene ratio lower than in said first etherification zone is maintained in said second etherification zone.

17. The process of claim 13 wherein said isomerization zone is maintained at a temperature of about 200° C. to 600° C., an olefin partial pressure between about 50 kPa and 500 kPa and WHSV between about 1.0 and 20; said isomerization zone catalyst has the structure selected from the group consisting of ZSM-22, ZSM-23, and ZSM-35; and said portion of said linear pentenes-rich higher boiling bottoms fraction is passed directly to said isomerization zone.

18. The process of claim 13 wherein said isomerization zone catalyst has the structure of ZSM-35.

* * * * *